US012588828B2

(12) United States Patent
Katz

(10) Patent No.: US 12,588,828 B2
(45) Date of Patent: Mar. 31, 2026

(54) METHODS AND SYSTEMS FOR DIAGNOSING AND TREATING FIBROMYALGIA

(71) Applicant: Robert S. Katz, Chicago, IL (US)

(72) Inventor: Robert S. Katz, Chicago, IL (US)

(*) Notice: Subject to any disclaimer, the term of this patent is extended or adjusted under 35 U.S.C. 154(b) by 1119 days.

(21) Appl. No.: 17/346,741

(22) Filed: Jun. 14, 2021

(65) Prior Publication Data

US 2021/0315472 A1     Oct. 14, 2021

Related U.S. Application Data

(63) Continuation of application No. 15/780,891, filed as application No. PCT/US2016/064597 on Dec. 2, 2016, now Pat. No. 11,039,755.

(Continued)

(51) Int. Cl.
*A61B 5/00*          (2006.01)
*A61B 5/03*          (2006.01)
(Continued)

(52) U.S. Cl.
CPC .............. *A61B 5/03* (2013.01); *A61B 5/1107* (2013.01); *A61B 5/224* (2013.01); *A61B 5/4519* (2013.01); *A61B 5/4839* (2013.01)

(58) Field of Classification Search
CPC ......... A61B 5/03; A61B 5/1107; A61B 5/224; A61B 5/4519; A61B 5/4839
See application file for complete search history.

(56) References Cited

U.S. PATENT DOCUMENTS 4,592,371 A * 6/1986 Pellicano ............... A61B 5/224
                                                    600/587
4,817,629 A 4/1989 Davis
(Continued)

FOREIGN PATENT DOCUMENTS

RU          2438721 C2     1/2012
RU          2560168 C2     8/2015
WO     2014018661 A1     1/2014

OTHER PUBLICATIONS

Schneider et al., "Commentary: Differential Diagnosis of Fibromyalgia Syndrome: Proposal of a Model and Algorithm for Patients Presenting with the Primary Symptom of Chronic Widespread Pain", Journal of Manipulative and Physiological Therapeutics, 29(6):493-501 (2006).

(Continued)

*Primary Examiner* — May A Abouelela
(74) *Attorney, Agent, or Firm* — McDonnell Boehnen Hulbert & Berghoff LLP

(57)          ABSTRACT
The present disclosure provides methods and systems for diagnosing and treating fibromyalgia in a patient. In one method, a pressure value is obtained for the patient, wherein the pressure value is determined by inserting a needle of a device into a location in the patient, injecting saline solution into the patient at the location, and measuring a pressure at the location; and fibromyalgia is diagnosed in the patient if the pressure at the location exceeds a threshold pressure value. The present disclosure also provides a device for use in the methods of the disclosure. One such device includes a needle, a syringe including a saline solution, a tube positioned between the syringe and the needle, and a pressure sensor configured to obtain a pressure value at a muscle location of a patient.

12 Claims, 2 Drawing Sheets

Related U.S. Application Data

(60) Provisional application No. 62/397,893, filed on Sep. 21, 2016, provisional application No. 62/396,054, filed on Sep. 16, 2016, provisional application No. 62/379,787, filed on Aug. 26, 2016, provisional application No. 62/262,432, filed on Dec. 3, 2015.

(51) Int. Cl.

| *A61B 5/11* | (2006.01) |
| *A61B 5/22* | (2006.01) |

(56)         References Cited

U.S. PATENT DOCUMENTS

| | | | | |
|---|---|---|---|---|
| 5,353,800 | A | 10/1994 | Pohndorf | |
| 5,553,514 | A * | 9/1996 | Walkowc | F16F 15/10 |
| | | | | 74/574.2 |
| 5,935,083 | A | 8/1999 | Williams | |
| 7,018,336 | B2 | 3/2006 | Enegren | |
| 8,814,807 | B2 | 8/2014 | Hulvershorn | |
| 9,358,038 | B2 | 6/2016 | Hulvershorn | |
| 9,888,881 | B2 | 2/2018 | Hulvershorn | |
| 10,405,797 | B1 * | 9/2019 | Uehara | A61B 5/1107 |
| 2005/0152905 | A1 * | 7/2005 | Omoigui | A61K 38/1793 |
| | | | | 514/420 |
| 2006/0004457 | A1 | 1/2006 | Collins | |
| 2006/0052729 | A1 * | 3/2006 | Gurses | A61H 23/02 |
| | | | | 600/557 |
| 2006/0116602 | A1 | 6/2006 | Alden | |
| 2006/0122488 | A1 | 6/2006 | Kajbafzadeh | |
| 2006/0122555 | A1 | 6/2006 | Hochman | |
| 2007/0005018 | A1 | 1/2007 | Tekbuchava | |
| 2007/0043120 | A1 * | 2/2007 | Beyreuther | A61K 31/165 |
| | | | | 514/616 |
| 2007/0048372 | A1 * | 3/2007 | Beyreuther | A61K 31/55 |
| | | | | 514/217 |
| 2007/0135736 | A1 | 6/2007 | Addington | |
| 2007/0191733 | A1 | 8/2007 | Gianchandani | |
| 2007/0197657 | A1 * | 8/2007 | Beyreuther | A61P 19/02 |
| | | | | 514/616 |
| 2008/0065002 | A1 | 3/2008 | Lobi | |
| 2009/0012421 | A1 | 1/2009 | Bek | |
| 2009/0247899 | A1 | 10/2009 | Dennison | |
| 2010/0094143 | A1 | 4/2010 | Mahapatra | |
| 2010/0106140 | A1 | 4/2010 | Odland | |
| 2010/0137736 | A1 | 6/2010 | Addington | |
| 2011/0060229 | A1 | 3/2011 | Hulvershorn | |
| 2011/0110862 | A1 * | 5/2011 | Nagakura | G01N 33/5088 |
| | | | | 800/9 |
| 2011/0230736 | A1 | 9/2011 | Tepper | |
| 2011/0264030 | A1 | 10/2011 | Desimone | |
| 2011/0313318 | A1 | 12/2011 | Rule | |
| 2012/0226334 | A1 | 9/2012 | Gardiner | |
| 2012/0253036 | A1 * | 10/2012 | Nagakura | A61K 31/551 |
| | | | | 540/593 |
| 2013/0165491 | A1 * | 6/2013 | Kiso | A61P 25/00 |
| | | | | 548/268.2 |
| 2014/0249151 | A1 * | 9/2014 | Kawakami | A61P 3/10 |
| | | | | 514/266.3 |
| 2015/0182747 | A1 * | 7/2015 | Ajiki | A61N 1/37264 |
| | | | | 607/48 |
| 2015/0258287 | A1 | 9/2015 | Shahaf | |
| 2015/0282753 | A1 | 10/2015 | Ahamdi | |
| 2015/0313512 | A1 | 11/2015 | Hausman | |
| 2016/0166735 | A1 | 6/2016 | Chang | |
| 2018/0028096 | A1 * | 2/2018 | Katz | A63B 24/0062 |
| 2018/0264317 | A1 * | 9/2018 | Yuan | A61B 5/22 |

OTHER PUBLICATIONS

Fibromyalgia pain Characteristics, retrieved from Internet <URL:http://pain-education.com/fibromyalgia-pain-characteristics.hmtl> Nov. 22, 2017.

Intramuscular Injection Guidelines for Needle Length and Gauge Selection. BD Helping all people live healthy lives (2012).

Mikkelsen et al., "Pressure Pain Threshold is Increased in Young Male Football Players when Using Shock Absorbing Insoles", Master thesis, sports science, abstract (2012).

Staud et al., "Analgesic and Anti-Hiperalgesic Effects of Muscle Injectiosn with Lidocaine or Saline in Patients with Fibromyalgia Syndrome", Eur J Pain, 18(6):803-812 (2014).

See et al., "Choosing a Skeletal Muscle Relaxant", American Family Physician, 78(3):365-370 (2008).

International Search Report and Written Opinion for corresponding PCT Application No. PCT/US2016/064597 dated Mar. 16, 2017.

Supplemental International Search Report for corresponding PCT Application No. PCT/US2016/064597 dated Dec. 22, 2017.

* cited by examiner

METHODS AND SYSTEMS FOR DIAGNOSING AND TREATING FIBROMYALGIA

CROSS-REFERENCE TO RELATED APPLICATIONS

This application is a continuation of U.S. Non-Provisional application Ser. No. 15/780,891 entitled "Methods and Systems for Diagnosing and Treating Fibromyalgia", filed on Jun. 1, 2018 that claims priority to (i) U.S. Provisional Application No. 62/262,432 entitled "Methods and Systems for Measuring Muscle Pressure," filed on Dec. 3, 2015, (ii) U.S. Provisional Application No. 62/379,787 entitled "Methods for Diagnosing and Treating Fibromyalgia," filed on Aug. 26, 2016, (iii) U.S. Provisional Application No. 62/396,054 entitled "Methods for Diagnosing and Treating Fibromyalgia," filed on Sep. 16, 2016, and (iv) U.S. Provisional Application No. 62/397,893 entitled "Methods for Diagnosing and Treating Fibromyalgia," filed on Sep. 21, 2016, all of which are hereby incorporated by reference in their entirety.

FIELD OF THE INVENTION

The present disclosure provides methods and systems for diagnosing and treating fibromyalgia in a patient. In one method, a pressure value is obtained for the patient, wherein the pressure value is determined by inserting a needle of a device into a location in the patient, injecting saline solution into the patient at the location, and measuring a pressure at the location; and fibromyalgia is diagnosed in the patient if the pressure at the location exceeds a threshold pressure value. The present disclosure also provides a device for use in the methods of the disclosure. One such device includes a needle, a syringe including a saline solution, a tube positioned between the syringe and the needle, and a pressure sensor configured to obtain a pressure value at a muscle location of a patient.

BACKGROUND OF THE INVENTION

Fibromyalgia is chronic widespread pain associated with insomnia, fatigue, and cognitive dysfunction. Surveys in the United States estimate that fibromyalgia affects approximately 2-8% of the adult population. Although there currently is no objective test for determining whether a patient suffers from fibromyalgia, a diagnosis of fibromyalgia has become much more credible since the American College of Rheumatology (ACR) defined the illness in 1990 using agreed-upon criteria. Nevertheless, approximately 25% of fibromyalgia patients still do not satisfy the ACR 1990 classification criteria (Wolfe et al., *Arthritis Care Res.* 62(5): 600-10 (2010)). Indeed, fibromyalgia may be associated with a significant percentage of the 10-12% of the U.S. population that suffers from chronic pain. In 2010, fibromyalgia criteria were changed, primarily because the requirement of having eleven tender points over a possible eighteen throughout the body was difficult to apply in practice. Also, these tender points vary from time to time and could not be relied on for a diagnosis of fibromyalgia, but the other criteria of widespread pain (up to nineteen areas throughout the body), poor sleep, fatigue, and cognitive symptoms, especially memory loss and concentration problems, were maintained as essential criteria for the diagnosis.

Although there are guidelines for the diagnosis of fibromyalgia, and clinicians generally agree about such a diagnosis, there remains no specific, reliable test for fibromyalgia. Currently, there is no single test that can fully diagnose fibromyalgia, and there is some debate over the symptoms that should be considered as essential diagnostic criteria and whether an objective diagnosis may be possible. Existing methods of diagnosing fibromyalgia typically use subjective pain values provided by the patient for several areas of the body. As such, one patient's score on such a test is difficult to compare with another patient's score since pain thresholds may vary from patient to patient. Therefore, an improved objective method for diagnosing fibromyalgia and evaluating treatment of patients with fibromyalgia is desired.

SUMMARY OF THE INVENTION

This disclosure is related to methods and systems for diagnosing fibromyalgia in a patient by measuring muscle tension.

In a first aspect, the disclosure relates to a method for diagnosing fibromyalgia in a patient comprising: obtaining a pressure value for the patient, wherein the pressure value is determined by inserting a needle of a device into a muscle location in the patient, injecting saline solution into the patient at the muscle location, and measuring a pressure value at the muscle location; and diagnosing fibromyalgia in the patient if the pressure value at the muscle location exceeds a threshold pressure value.

In a second aspect, the disclosure relates to a method for treating fibromyalgia in a patient comprising: obtaining a pressure value for the patient, wherein the pressure value is determined by inserting a needle of a device into a muscle location in the patient, injecting saline solution into the patient at the muscle location, and measuring a pressure value at the muscle location; and administering an effective amount of a muscle relaxant to the patient if the pressure at the muscle location exceeds a threshold pressure value.

In a third aspect, the disclosure relates to a method of detecting a pressure value of a muscle location in a patient suspected of having fibromyalgia comprising: obtaining a pressure value for the patient, wherein the pressure value is determined by inserting a needle of a device into a muscle location in the patient, injecting saline solution into the patient at the muscle location, and measuring a pressure value at the muscle location; and diagnosing fibromyalgia in the patient if the pressure at the muscle location exceeds a threshold pressure value.

In a fourth aspect, the disclosure relates to a method for diagnosing and treating fibromyalgia in a patient comprising: obtaining a pressure value for the patient, wherein the pressure value is determined by inserting a needle of a device into a muscle location in the patient, injecting saline solution into the patient at the muscle location, and measuring a pressure value at the muscle location; diagnosing fibromyalgia in the patient if the pressure at the muscle location exceeds a threshold pressure value; and administering an effective amount of a muscle relaxant to the diagnosed patient if the pressure at the muscle location exceeds a threshold pressure value.

In a fifth aspect, the disclosure relates to a device comprising: a needle; a syringe including a saline solution; a tube positioned between the syringe and the needle; and a pressure sensor configured to obtain a pressure value at a muscle location of a patient.

These as well as other aspects, advantages, and alternatives will become apparent to those of ordinary skill in the art by reading the following detailed description.

DETAILED DESCRIPTION OF THE INVENTION

Figure 1:
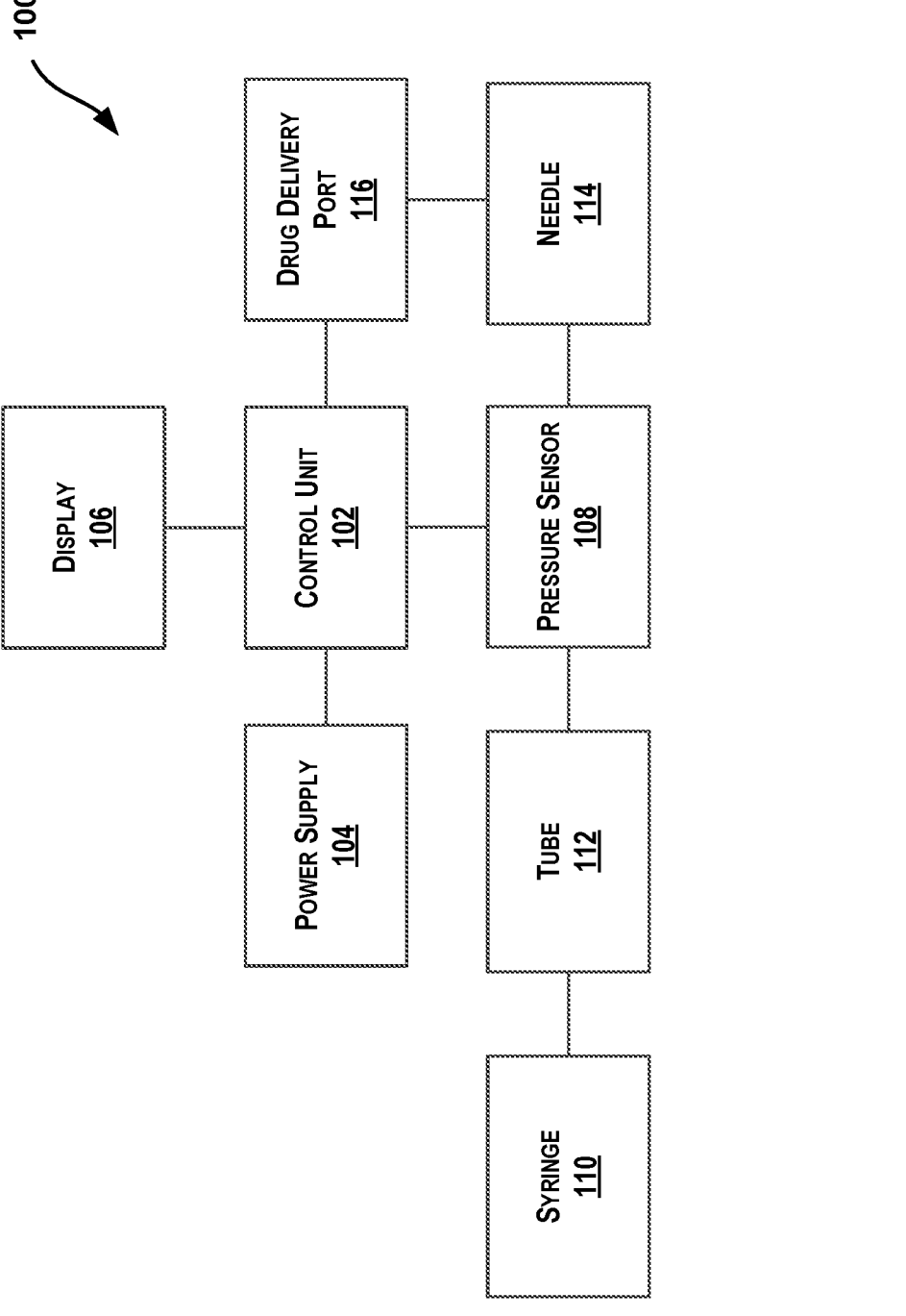
FIG. 1 is a simplified block diagram of a device for measuring muscle pressure, according to an example embodiment.

Currently, there is no single test that can fully diagnose fibromyalgia, and there is debate over the symptoms that should be considered as essential diagnostic criteria and whether an objective diagnosis may be possible. Existing methods of diagnosing fibromyalgia typically use subjective pain values provided by the patient for several areas of the body. As such, one patient's score on such a test is difficult to compare with another patient's score since pain thresholds may vary from patient to patient. Therefore, an improved objective method for diagnosing fibromyalgia and evaluating treatment of patients with fibromyalgia is desired.

The inventors have discovered that patients with fibromyalgia have significantly increased intramuscular pressure. Furthermore, the inventors have determined that fibromyalgia patients have tender muscles and dolorimetry scores were low, indicating decreased tolerance for manually applied pressure. The amount of muscle tenderness correlated with the muscle pressure. The pain in fibromyalgia may be related to increased muscle pressure and tension. Fibromyalgia patients may be unconsciously tightening their muscles. Though pain centers in the brain activate quickly (central sensitization) in fibromyalgia patients when pressure is applied to the muscles, this finding may be due to increased muscle tenderness and elevated muscle pressure in fibromyalgia patients. The inventors have determined methods for diagnosing fibromyalgia in a patient by at least measuring muscle pressure and/or tension.

In one aspect, the invention provides a method for diagnosing fibromyalgia in a patient comprising obtaining a pressure value for a patient to be diagnosed with and/or treated for fibromyalgia, wherein the pressure value is determined by inserting a needle of a device into a muscle location in the patient, injecting saline solution into the patient at the muscle location, and measuring a pressure value at the muscle location; and diagnosing fibromyalgia in the patient if the pressure value at the muscle location exceeds a threshold pressure value.

In another aspect, the invention provides a method for treating fibromyalgia in a patient comprising: obtaining a pressure value for the patient, wherein the pressure value is determined by inserting a needle of a device into a muscle location in the patient, injecting saline solution into the patient at the muscle location, and measuring a pressure value at the muscle location; and administering an effective amount of a muscle relaxant to the patient if the pressure at the muscle location exceeds a threshold pressure value.

In another aspect, the disclosure relates to a method for diagnosing and treating fibromyalgia in a patient comprising: obtaining a pressure value for the patient, wherein the pressure value is determined by inserting a needle of a device into a muscle location in the patient, injecting saline solution into the patient at the muscle location, and measuring a pressure value at the muscle location; diagnosing fibromyalgia in the patient if the pressure at the muscle location exceeds a threshold pressure value; and administering an effective amount of a muscle relaxant to the diagnosed patient if the pressure at the muscle location exceeds a threshold pressure value.

In another aspect, the invention provides a method of detecting a pressure value of a muscle location in a patient suspected of having fibromyalgia comprising: obtaining a pressure value for the patient, wherein the pressure value is determined by inserting a needle of a device into a muscle location in the patient, injecting saline solution into the patient at the muscle location, and measuring a pressure value at the muscle location; and diagnosing fibromyalgia in the patient if the pressure at the muscle location exceeds a threshold pressure value.

In yet another aspect, the invention provides a device comprising: a needle; a syringe including a saline solution; a tube positioned between the syringe and the needle; and a pressure sensor configured to obtain a pressure value at a muscle location of a patient.

The pressure value for the patient may be determined by inserting a needle of a device into a muscle location in the patient. In an embodiment, the muscle location can be any muscle of the patient, such as the trapezius muscle, biceps brachii, triceps brachii muscle, pectoralis major muscle, deltoideus muscle, gastrocnemius muscle, soleus muscle, quadriceps femoris muscle, gluteus maximus muscle or rectus femoris muscle of the patient. In an embodiment, the muscle location is the trapezius muscle.

In an embodiment, the method includes injecting saline solution into the patient at the muscle location. The saline solution forms a pressure transmitting pocket at the tip of the needle. In certain embodiments, the terms "saline solution" or "saline" can refer to a sterile solution of sodium chloride (NaCl) in water. The concentrations of salt in the saline solution can vary; however, a saline solution typically contains 9.0 g of salt (NaCl) per liter or water (0.90% w/v). In some embodiments, between 0.1 and 1.0 cubic centimeters (cc) of saline solution is injected into the patient at the muscle location. In another embodiment, 0.3 cc of saline solution is injected into the patient. The method can include measuring a pressure at the muscle location. The pressure can be measured via a pressure sensor of the device.

In another embodiment, the method includes, in response to a determination that the pressure value at the muscle location exceeds a threshold pressure value, determining that the patient has fibromyalgia. In yet another embodiment, the threshold pressure value is between 5 and 60 millimeters of mercury (mmHg) or between 10 and 50, or between 20 and 40 mmHg. In an embodiment, the threshold pressure value is 20 mmHg. As such, if the pressure at the location exceeds 20 mmHg, for example, a physician may determine that the patient has fibromyalgia.

In an additional embodiment, the method can further include: (i) obtaining a pressure value for the patient from a second muscle location, wherein the pressure value is determined by inserting the needle of the device into a second muscle location in the patient, injecting saline solution into the patient at the second muscle location, and measuring a pressure value at the second muscle location, (ii) determining an average pressure value based on the pressure value measured at the first muscle location and the pressure value measured at the second muscle location, and (iii) diagnosing fibromyalgia in the patient if the average pressure value exceeds the threshold pressure value. The method can further include measuring the muscle pressure at additional muscle locations as well, and combining each measured pressure value to determine an average pressure value with which to compare with the threshold pressure value.

In another example, the method can further include using the measured pressure value at the location to associate the patient with one of a plurality of muscle tenderness categories. One or more of the plurality of muscle tenderness categories could be mild muscle tenderness, moderate muscle tenderness, and severe or extreme muscle tenderness. Other categories are possible as well. For example, if a patient has a measured muscle pressure value greater than approximately 20 mmHg but less than approximately 29 mmHg, the patient can fall in the mild muscle tenderness category. In another example, a patient has a measured muscle pressure value greater than approximately 29 mmHg but less than approximately 34 mmHg, the patient can fall in the moderate muscle tenderness category. In yet another example, if a patient has a measured muscle pressure value greater than approximately 34 mmHg, the patient can fall in the extreme muscle tenderness category. A treating physician may then use the category information to determine a proper treatment plan for the patient. For example, a patient may receive a higher dosage of a medication if he or she falls into the extreme muscle tenderness category.

In yet another embodiment, the method comprises a first needle, and the pressure value measured at the muscle location in the method comprises a first pressure value. In such an example, the method continues by providing a medication to the patient. In an embodiment, the medication can be a muscle relaxant. In another embodiment, the method includes obtaining a second pressure value from the patient from a second muscle location by inserting a second needle of the device into the second muscle location in the patient, and measuring a second pressure value at the second muscle location; and comparing the first pressure value to the second pressure value to determine whether the pressure at the second muscle location has been reduced. As discussed above, the needles may be configured to be removably attached to the rest of the device such that a new needle may be attached to the device after each use. The saline solution forms a pressure transmitting pocket at the tip of the needle. In one example, 0.3 cc of saline solution is injected into the patient at the location, and the method includes measuring a second pressure at the location. The pressure may be measured via a pressure sensor of the device, as discussed above.

In an embodiment, the method can further include, in response to a determination that the second pressure value at the location no longer exceeds the threshold pressure value, decreasing a dosage of the medication provided to the patient. In another embodiment, the method can further include, in response to a determination that the second pressure value at the location still exceeds the threshold pressure value, increasing a dosage of the medication provided to the patient. In yet another embodiment, the method can further include, in response to a determination that the second pressure at the location still exceeds the threshold pressure value, maintaining a dosage of the medication provided to the patient.

In some embodiments, the methods can include treating a patient with a muscle relaxant. In an embodiment, the method for treating fibromyalgia can result in the amelioration of muscle pressure or muscle tension, muscle fatigue, or pain associated with fibromyalgia. The methods can comprise administering to the patient a therapeutically effective amount of a muscle relaxant. Muscle relaxants are known in the art and can include, but are not limited to, baclofen, carisoprodol (SOMA®), chlorzoxazone (PARAFON FORTE DSC®), cyclobenzaprine (FLEXERIL®, FEXMID®, AMRIX®), dantrolene (DAN- TRIUM®), metaxalone (SKELAXIN®), methocarbamol (ROBAXIN®), orphenadrine (NORFLEX®) or tizanidine (ZANAFLEX®). In another embodiment, the muscle relaxant is administered in a tablet dosage form. The tablet dosage form can comprise an amount of a muscle relaxant, or a pharmaceutically acceptable equivalent thereof, that can be 1 mg, 5 mg, 10 mg, 15 mg, 20 mg, 25 mg, 30 mg, 35 mg, 40 mg, 45 mg, 50 mg, 55 mg, 60 mg 65 mg, 70 mg, 75 mg, 80 mg, 85 mg, 90 mg, 95 mg, 100 mg, 125 mg, 150 mg, 175 mg, 200 mg, 250 mg, 300 mg, 350 mg, 400 mg, 450 mg, 500 mg, 600 mg, 700 mg, 750 mg, 800 mg, 900 mg, or 1000 mg. In some embodiments, the muscle relaxant is administered in a tablet dosage form one to four times daily, and can be administered at least once a day for at least four weeks. In other embodiments, the muscle relaxant can be in the form of a modified release formulation.

In other embodiments, the methods can include treating a patient with an antidepressant. In an embodiment, the method for treating fibromyalgia can result in the amelioration of muscle pressure or muscle tension, muscle fatigue, pain or other symptoms associated with fibromyalgia. The methods can comprise administering to the patient a therapeutically effective amount of an antidepressant. Antidepressants are known in the art and can include, but are not limited to, ABILIFY® (ariprazole), ADAPIN® (doxepin), ANAFRANIL® (clomipramine), APLENZIN® (bupropion), ASENDIN® (amoxapine), AVENTYL HCI® (nortriptyline), BRINTELLIX® (vortioxetine), CELEXA® (citalopram), CYMBALTA® (duloxetine), DESYREL® (trazodone), EFFEXOR XR® (venlafaxine), EMSAM® (selegiline), ETRAFON® (perphenazine and amitriptyline), ELAVIL® (amitriptyline), ENDEP® (amitriptyline), FETZIMA® (levomilnacipran), KHEDEZLA® (desvenlafaxine), LATUDA® (lurasidone), LAMICTAL® (lamotrigine), LEXAPRO® (escitalopram), LIMBITROL® (amitriptyline and chlordiazepoxide), MARPLAN (isocarboxazid), NARDIL® (phenelzine), NORPRAMIN® (desipramine), OLEPTRO® (trazodone), PAMELOR® (nortriptyline), PARNATE® (tranylcypromine), PAXIL® (paroxetine), PEXEVA® (paroxetine), PROZAC® (fluoxetine), PRISTIQ® (desvenlafaxine), REMERON® (mirtazapine), SARAFEM® (fluoxetine), SEROQUEL XR® (quetiapine), SERZONE® (nefazodone), SINEQUAN® (doxepin), SURMONTIL® (trimipramine), SYMBYAX® (fluoxetine and the atypical antipsychotic drug olanzapine), TOFRANIL® (imipramine), TRIAVIL® (perphenazine and amitriptyline), VIIBRYD® (vilazodone), VIVACTIL® (protriptyline), WELLBUTRIN® (bupropion), ZOLOFT® (sertraline), or ZYPREXA® (olanzapine). In another embodiment, the antidepressant can be administered in a tablet dosage form. The tablet dosage form can comprise an amount of a antidepressant, or a pharmaceutically acceptable equivalent thereof, that can be 1 mg, 5 mg, 10 mg, 15 mg, 20 mg, 25 mg, 30 mg, 35 mg, 40 mg, 45 mg, 50 mg, 55 mg, 60 mg 65 mg, 70 mg, 75 mg, 80 mg, 85 mg, 90 mg, 95 mg, 100 mg, 125 mg, 150 mg, 175 mg, 200 mg, 250 mg, 300 mg, 350 mg, 400 mg, 450 mg, 500 mg, 600 mg, 700 mg, 750 mg, 800 mg, 900 mg, or 1000 mg. In some embodiments, the antidepressant is administered in a tablet dosage form one to four times daily, and can be administered at least once a day for at least four weeks. In other embodiments, the antidepressant can be in the form of a modified release formulation.

With reference to the Figures, FIG. 1 illustrates an example device 100 for measuring muscle pressure. In particular, as described above, the device 100 may be used to obtain a pressure value for a patient. In particular, the device 100 may be used to measure the muscle pressure for a particular muscle location, the trapezius muscle, biceps brachii, triceps brachii muscle, pectoralis major muscle, deltoideus muscle, gastrocnemius muscle, soleus muscle, quadriceps femoris muscle, gluteus maximus muscle or rectus femoris muscle of the patient. In an embodiment, the muscle location is the trapezius muscle. The device 100 may include a control unit 102 coupled to a power supply 104 and a display 106. The control unit 102 may be further coupled to a pressure sensor 108. The pressure sensor 108 is configured to obtain a pressure value at a muscle location of a patient, as discussed above.

The device 100 may further include a syringe 110 and a tube 112 coupling the syringe 110 to a needle 114. In one example, the pressure sensor 108 may be positioned between the tube 112 and the needle 114. In some embodiments, the needle comprises a needle size that can be between a 7 gauge needle and a 34 gauge needle, a 10 gauge needle and a 30 gauge needle, a 15 gauge needle and a 25 gauge needle, or a 20 gauge needle and a 23 gauge needle (see Table 1). In one embodiment, the needle is a 22 gauge needle. In some embodiments, the needle length is between 5 mm and 100 mm. For example, the needle length can be 6 mm, 8 mm, 12.7 mm, 20 mm, 30 mm, 40 mm, 50 mm, 60 mm, 70 mm, 80 mm, 90 mm or 100 mm. In another embodiment, the needle can be 1-8 inches long. For example, the needle length can be 1 inch, 2 inches, 3 inches, 3.5 inches, 4 inches, 5 inches, 6 inches, 7 inches or 8 inches.

TABLE 1

Exemplary needle gauges.

| Needle Gauge | Nominal outer diameter | | | Nominal inner diameter | | | Nominal wall thickness | | |
|---|---|---|---|---|---|---|---|---|---|
| | inches | mm | tol. inches (mm) | inches | mm | tol. inches (mm) | inches | mm | tol. inches (mm) |
| 7 | 0.180 | 4.572 | ±0.001 (±0.025) | 0.150 | 3.810 | ±0.003 (±0.076) | 0.015 | 0.381 | ±0.001 (±0.025) |
| 8 | 0.165 | 4.191 | ±0.001 (±0.025) | 0.135 | 3.429 | ±0.003 (±0.076) | 0.015 | 0.381 | ±0.001 (±0.025) |
| 9 | 0.148 | 3.759 | ±0.001 (±0.025) | 0.118 | 2.997 | ±0.003 (±0.076) | 0.015 | 0.381 | ±0.001 (±0.025) |
| 10 | 0.134 | 3.404 | ±0.001 (±0.025) | 0.106 | 2.692 | ±0.003 (±0.076) | 0.014 | 0.356 | ±0.001 (±0.025) |
| 11 | 0.120 | 3.048 | ±0.001 (±0.025) | 0.094 | 2.388 | ±0.003 (±0.076) | 0.013 | 0.330 | ±0.001 (±0.025) |
| 12 | 0.109 | 2.769 | ±0.001 (±0.025) | 0.085 | 2.159 | ±0.003 (±0.076) | 0.012 | 0.305 | ±0.001 (±0.025) |
| 13 | 0.095 | 2.413 | ±0.001 (±0.025) | 0.071 | 1.803 | ±0.003 (±0.076) | 0.012 | 0.305 | ±0.001 (±0.025) |
| 14 | 0.083 | 2.108 | ±0.001 (±0.025) | 0.063 | 1.600 | ±0.003 (±0.076) | 0.01 | 0.254 | ±0.001 (±0.025) |
| 15 | 0.072 | 1.829 | ±0.0005 (±0.013) | 0.054 | 1.372 | ±0.0015 (±0.038) | 0.009 | 0.229 | ±0.0005 (±0.013) |
| 16 | 0.065 | 1.651 | ±0.0005 (±0.013) | 0.047 | 1.194 | ±0.0015 (±0.038) | 0.009 | 0.229 | ±0.0005 (±0.013) |
| 17 | 0.058 | 1.473 | ±0.0005 (±0.013) | 0.042 | 1.067 | ±0.0015 (±0.038) | 0.008 | 0.203 | ±0.0005 (±0.013) |
| 18 | 0.050 | 1.270 | ±0.0005 (±0.013) | 0.033 | 0.838 | ±0.0015 (±0.038) | 0.0085 | 0.216 | ±0.0005 (±0.013) |
| 19 | 0.042 | 1.067 | ±0.0005 (±0.013) | 0.027 | 0.686 | ±0.0015 (±0.038) | 0.0075 | 0.191 | ±0.0005 (±0.013) |
| 20 | 0.03575 | 0.9081 | ±0.00025 (±0.0064) | 0.02375 | 0.603 | ±0.00075 (±0.019) | 0.006 | 0.1524 | ±0.00025 (±0.0064) |
| 21 | 0.03225 | 0.8192 | ±0.00025 (±0.0064) | 0.02025 | 0.514 | ±0.00075 (±0.019) | 0.006 | 0.1524 | ±0.00025 (±0.0064) |
| 22 | 0.02825 | 0.7176 | ±0.00025 (±0.0064) | 0.01625 | 0.413 | ±0.00075 (±0.019) | 0.006 | 0.1524 | ±0.00025 (±0.0064) |
| 22s | 0.02825 | 0.7176 | ±0.00025 (±0.0064) | 0.006 | 0.152 | ±0.00075 (±0.019) | 0.0111 | 0.2826 | ±0.00025 (±0.0064) |
| 23 | 0.02525 | 0.6414 | ±0.00025 (±0.0064) | 0.01325 | 0.337 | ±0.00075 (±0.019) | 0.006 | 0.1524 | ±0.00025 (±0.0064) |
| 24 | 0.02225 | 0.5652 | ±0.00025 (±0.0064) | 0.01225 | 0.311 | ±0.00075 (±0.019) | 0.005 | 0.1270 | ±0.00025 (±0.0064) |
| 25 | 0.02025 | 0.5144 | ±0.00025 (±0.0064) | 0.01025 | 0.260 | ±0.00075 (±0.019) | 0.005 | 0.1270 | ±0.00025 (±0.0064) |
| 26 | 0.01825 | 0.4636 | ±0.00025 (±0.0064) | 0.01025 | 0.260 | ±0.00075 (±0.019) | 0.004 | 0.1016 | ±0.00025 (±0.0064) |
| 26s | 0.01865 | 0.4737 | ±0.00025 (±0.0064) | 0.005 | 0.127 | ±0.00075 (±0.019) | 0.0068 | 0.1734 | ±0.00025 (±0.0064) |
| 27 | 0.01625 | 0.4128 | ±0.00025 (±0.0064) | 0.00825 | 0.210 | ±0.00075 (±0.019) | 0.004 | 0.1016 | ±0.00025 (±0.0064) |
| 28 | 0.01425 | 0.3620 | ±0.00025 (±0.0064) | 0.00725 | 0.184 | ±0.00075 (±0.019) | 0.0035 | 0.0889 | ±0.00025 (±0.0064) |
| 29 | 0.01325 | 0.3366 | ±0.00025 (±0.0064) | 0.00725 | 0.184 | ±0.00075 (±0.019) | 0.003 | 0.0762 | ±0.00025 (±0.0064) |
| 30 | 0.01225 | 0.3112 | ±0.00025 (±0.0064) | 0.00625 | 0.159 | ±0.00075 (±0.019) | 0.003 | 0.0762 | ±0.00025 (±0.0064) |
| 31 | 0.01025 | 0.2604 | ±0.00025 (±0.0064) | 0.00525 | 0.133 | ±0.00075 (±0.019) | 0.0025 | 0.0635 | ±0.00025 (±0.0064) |

TABLE 1-continued

Exemplary needle gauges.

| Needle Gauge | Nominal outer diameter | | | Nominal inner diameter | | | Nominal wall thickness | | |
|---|---|---|---|---|---|---|---|---|---|
| | inches | mm | tol. inches (mm) | inches | mm | tol. inches (mm) | inches | mm | tol. inches (mm) |
| 32 | 0.00925 | 0.2350 | ±0.00025 (±0.0064) | 0.00425 | 0.108 | ±0.00075 (±0.019) | 0.0025 | 0.0635 | ±0.00025 (±0.0064) |
| 33 | 0.00825 | 0.2096 | ±0.00025 (±0.0064) | 0.00425 | 0.108 | ±0.00075 (±0.019) | 0.002 | 0.0508 | ±0.00025 (±0.0064) |
| 34 | 0.00725 | 0.1842 | ±0.00025 (±0.0064) | 0.00325 | 0.0826 | ±0.00075 (±0.019) | 0.002 | 0.0508 | ±0.00025 (±0.0064) |

The syringe 110 may define a chamber configured to hold a liquid. In one example, such a chamber of the syringe 110 may hold a saline solution. Further, the needle 114 may be configured to be removably attached to the tube 112 such that a new needle may be attached to the tube 112 after each use. The control unit 102 may be configured to provide for display the determined pressure value at the muscle location of the patient on the display 106.

In operation, the site (e.g., the skin of the patient) above the muscle location is cleaned using standard surgical skin prep techniques. A plunger on the syringe 110 is depressed to force a saline solution out of the syringe 110 and out of the needle 114, thereby flushing out any excess air from the needle 114. The device 100 is then positioned above the skin at the point of entry at an angle approximating the final angle of the device 100 after introduction of the needle 114 into the target location. A zero button on the display 106 is pressed to zero out the system and eliminate any pressure differential due to the difference in height of the needle 114 and the pressure sensor 108. The needle 114 is then introduced into the target location and an appropriate amount of saline solution is injected into the target location to form a pressure transmitting pocket at the tip of the needle 114. The pressure at the location can then be read out by the pressure sensor 108 and displayed on display 106. After the pressure is read, the needle 114 is withdrawn from the location. Subsequent measurements in the same or other locations of the same patient can be made with the same needle using the same procedure, or a new needle can be used for each measurement.

In another embodiment, the control unit 102 may be further configured to compare the pressure value at the muscle location to a threshold pressure value. As discussed above, the threshold pressure value is between 5 and 60 millimeters of mercury (mmHg) or between 10 and 50, or between 20 and 40 mmHg. In an embodiment, the threshold pressure value is 20 mmHg. In one embodiment, the control unit 102 may be further configured to provide for display an indication that the patient has fibromyalgia if the comparison indicates that the pressure value at the muscle location exceeds the threshold pressure value. In another embodiment, the control unit 102 may be further configured to provide for display an indication that the patient does not have fibromyalgia if the comparison indicates that the pressure value at the muscle location does not exceed the threshold pressure value. In yet another embodiment, the control unit 102 may be further configured to use the measured pressure value at the muscle location to associate the patient with one of a plurality of muscle tenderness categories. In one embodiment, the plurality of muscle tenderness categories comprises three categories of mild, moderate, or extreme muscle tenderness.

In one embodiment, the device 100 further includes a drug delivery port 116 positioned between the needle 114 and the pressure sensor 108. The drug delivery port 116 is configured to provide a medicament to the muscle location through the needle 114. The drug delivery port 116 enables the same needle 114 to be used both to (i) determine the pressure value at the muscle location, and (ii) provide a medicament to the muscle location. As discussed above, the medicament may include a muscle relaxant. In one embodiment, the control unit 102 may be further configured to administer an effective amount of a muscle relaxant to the patient through the drug delivery port if the pressure at the muscle location exceeds a threshold pressure value.

In another embodiment, the control unit 102 may be further configured to (i) obtain a second pressure value from the patient from the muscle location, and (ii) compare the first pressure value to the second pressure value to determine whether the pressure at the muscle location has been reduced. In response to a determination that the second pressure value at the muscle location no longer exceeds the threshold pressure value, the control unit 102 may be further configured to decrease a dosage of the medication provided to the patient. In response to a determination that the second pressure value at the muscle location still exceeds the threshold pressure value, the control unit 102 may be configured to increase a dosage of the medication provided to the patient. In response to a determination that the second pressure value at the muscle location still exceeds the threshold pressure value, the control unit 102 may be further configured to maintain a dosage of the medication provided to the patient.

Figure 2:
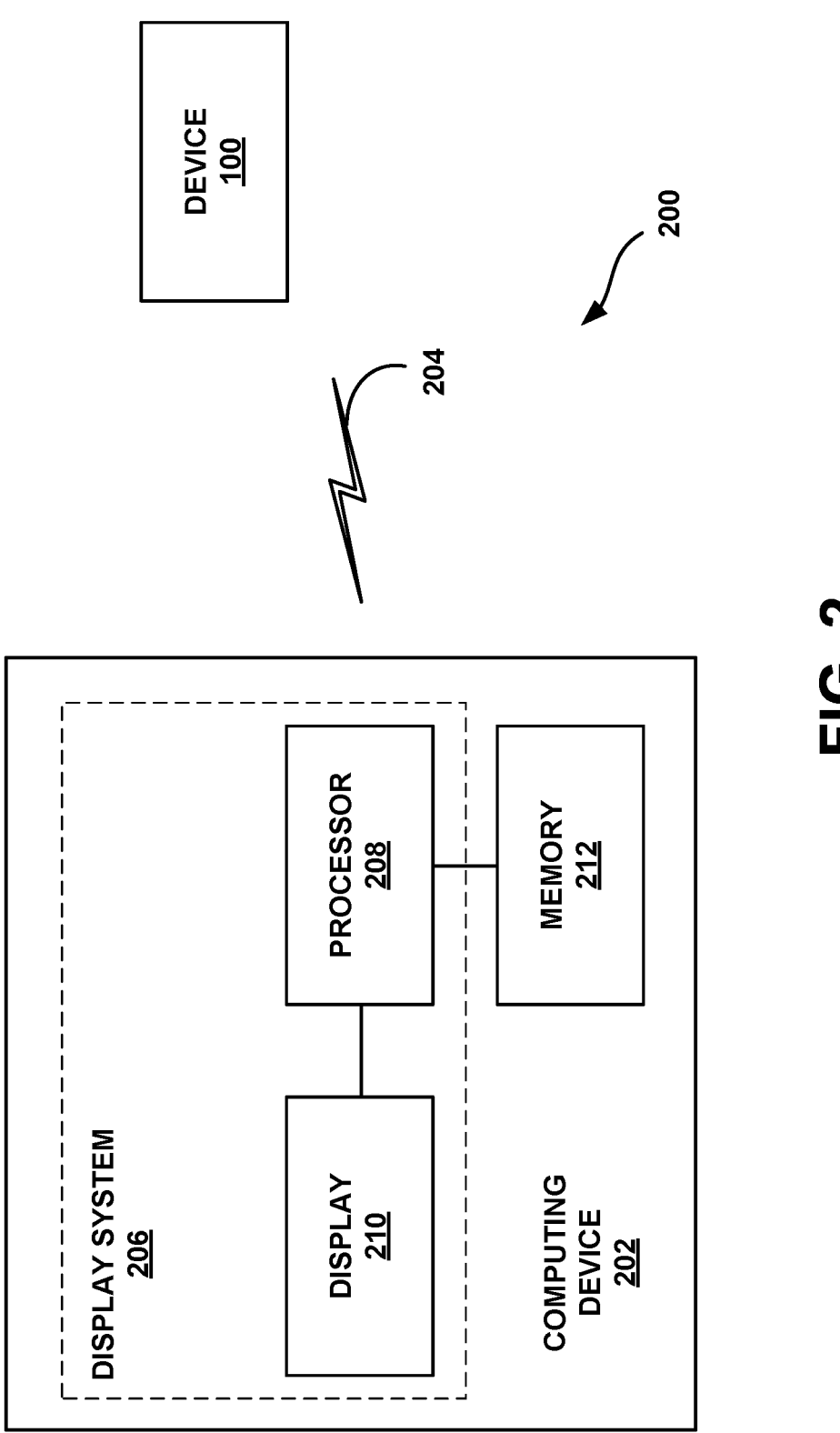
FIG. 2 is a schematic drawing of a computer network infrastructure, according to an example embodiment.

FIG. 2 illustrates an example schematic drawing of a computer network infrastructure. In one system 200, a computing device 202 communicates with the device 100 using a communication link 204, such as a wired or wireless connection. The computing device 202 may be any type of device that can receive data and display information corresponding to or associated with the data. For example, the computing device 202 may be a mobile phone, a tablet, or a personal computer as examples.

Thus, the computing device 202 may include a display system 206 comprising a processor 208 and a display 210. The display 210 may be, for example, an optical see-through display, an optical see-around display, or a video see-through display. The processor 208 may receive data from the device 100, and configure the data for display on the display 210. For example, processor 208 may receive muscle pressure data from device 100, and configure the data for display on the display 210. Depending on the desired configuration, processor 208 can be any type of processor including, but not limited to, a microprocessor, a microcontroller, a digital signal processor, or any combination thereof.

The computing device 202 may further include on-board data storage, such as memory 212 coupled to the processor 208. The memory 212 may store software that can be accessed and executed by the processor 208, for example. Further, processor 208 may receive data from the device 100, and configure the data for storage in the memory 212. For example, processor 208 may receive muscle pressure data from device 100, and configure the data for storage in the memory 212. The memory 212 can include any type of memory now known or later developed including but not limited to volatile memory (such as RAM), non-volatile memory (such as ROM, flash memory, etc.) or any combination thereof.

According to an example embodiment, the computing device 202 may include program instructions that are stored in the memory 212 (and/or possibly in another data-storage medium) and executable by the processor 208 to facilitate the various functions described herein. Although various components of the system 200 are shown as distributed components, it should be understood that any of such components may be physically integrated and/or distributed according to the desired configuration of the computing system.

The device 100 and the computing device 200 may contain hardware to enable the communication link 204, such as processors, transmitters, receivers, antennas, etc. In FIG. 2, the communication link 204 is illustrated as a wireless connection; however, wired connections may also be used. For example, the communication link 204 may be a wired link via a serial bus such as a universal serial bus or a parallel bus. A wired connection may be a proprietary connection as well. The communication link 204 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities.

GENERAL DEFINITIONS

As utilized in accordance with the present disclosure, the following terms, unless otherwise indicated, shall be understood to have the following meanings. Unless otherwise required by context, singular terms shall include pluralities and plural terms shall include the singular.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

The term "patient" as used herein refers to a human subject.

A "disease" or "disorder" is any condition that would benefit from treatment using the methods or compositions of the invention. "Disease," "disorder," and "condition" are used interchangeably herein and include chronic and acute disorders or diseases.

The term "treat" as used herein refers to both therapeutic treatment and prophylactic or preventative measures. The term "treatment" as used herein refers to the alleviation of symptoms of a disease. Those in need of treatment include those having the disorder as well as those prone to have the disorder or those in which the disorder is to be prevented.

The terms "composition," "therapeutic composition," or "pharmaceutical composition" as used herein refer to a compound or composition capable of inducing a desired therapeutic effect when properly administered to a patient.

The term "therapeutically acceptable" as used herein refers to one or more formulation materials suitable for accomplishing or enhancing the delivery of a composition of the invention.

The term "functional improvement" as used herein refers to a partial and/or complete, but in any case, significant improvement or restoration of at least one aspect of normal function to a state observed before onset of fibromyalgia symptoms. This is determined for each patient, e.g., by comparing the functional improvement following drug treatment with reference to the functional efficiency in a healthy population or before onset of fibromyalgia symptoms. Typically, the determination of improvement in one or more features of fibromyalgia recognized by the American College of Rheumatology (ACR) criteria for diagnosis (e.g., dyscognition, fatigue, pain, energy, mood, muscle pain, irritable bowel syndrome, thinking or remembering problems, muscle weakness, headache, numbness/tingling, dizziness, insomnia, and depression) will be indicative of overall functional improvement. Most tests combine one or more of these aspects of features of fibromyalgia. Functional restoration or improvement of features of fibromyalgia can for instance be evaluated and/or quantified using the Health Assessment Questionnaire (HAQ), which is a short measurement questionnaire regarding patient function. HAQ scores are calculated based on a patient checking a short form about the activities of daily living that the patient is able to do. Additionally, the degree of functional improvement or restoration is measured using a Widespread Pain Index or Symptom Severity scale score. Additionally or alternatively, the degree of functional improvement or restoration can be measured using the methods as disclosed herein (e.g., determining that the pressure value at the muscle location of a patient has decreased or is below a threshold pressure value following treatment). Functional improvement can prevent disability as many fibromyalgia patients conclude that they can no longer work due to fatigue, cognitive problems, and pain.

The terms "pain scale" and "pain score" as used herein refer to one or more scaling or scoring systems typically used to rate a pain level in a patient. Typically, the pain scaling or pain scoring schemes rank pain from 0-10 (0=no pain, and 10=worst pain imaginable). For example, a score of zero would be no pain, a score from 1-3 would be mild pain (e.g., nagging, annoying, interfering little with daily life activities), a score between 4-6 would be moderate pain (e.g., interferes significantly with daily life activities), and a score between 7-10 would be severe pain (e.g., disabling; unable to perform daily life activities).

The terms "dolorimetry score" or "dolorimetry reading" as used herein refer to one or more ranking schemes used to measure a pain sensitivity or pain intensity in a patient. Dolorimetry can be measured by known methods readily available to those of skill in the art. For example, dolorimeter devices can apply steady pressure, heat, or electrical stimulation to some area, or move a joint or other body part and determine what level of heat or pressure or electric current or amount of movement produces a sensation of pain. Sometimes the pressure can be applied using a blunt object, or by locally increasing the air pressure on some area of the body, and sometimes by pressing a sharp instrument against the body. For example, if a dolorimeter device applies a steady pressure that gradually increases between, for example, 0 and 30 pounds, then as the dolorimeter device gradually increases the steady pressure on a body part, the point at which a patient indicates a sensation of pain is the dolorimetry score or dolorimetry reading (e.g. a sensation of pain at 8 pounds, is a score of 8).

The terms "muscle tenderness" or "tenderness" as used herein refer to one or more ranking schemes used to measure a pain sensitivity in a muscle of a patient. Tenderness can be scored by known methods readily available to those of skill in the art. For example, muscle tenderness can be scored on a scale of 0 to 3, wherein 0 is no tenderness, 1 is mild tenderness, 2 is moderate tenderness and 3 is severe tenderness. As such, one or more of a plurality of muscle tenderness categories could be mild muscle tenderness, moderate muscle tenderness, and severe muscle tenderness. Other categories of tenderness are possible as well.

Without limiting the present disclosure, a number of embodiments of the present disclosure are described below for purpose of illustration.

Embodiment 1: A method for diagnosing fibromyalgia in a patient comprising:
(a) obtaining a pressure value for the patient, wherein the pressure value is determined by inserting a needle of a device into a muscle location in the patient, injecting saline solution into the patient at the muscle location, and measuring a pressure value at the muscle location; and
(b) diagnosing fibromyalgia in the patient if the pressure value at the muscle location exceeds a threshold pressure value.

Embodiment 2: The method of embodiment 1, wherein the needle has a gauge of between 10 and 30.

Embodiment 3: The method of embodiment 2, wherein the gauge of the needle is 22.

Embodiment 4: The method of any one of embodiments 1-3, wherein the threshold pressure value is between 5 and 60, between 10 and 50, or between 20 and 40 millimeters of mercury (mmHg).

Embodiment 5: The method of embodiment 4, wherein the threshold pressure value is 20 millimeters of mercury (mmHg).

Embodiment 6: The method of any one of embodiments 1-5, wherein the muscle location in the patient is a trapezius muscle, biceps brachii muscle, triceps brachii muscle, pectoralis major muscle, deltoideus muscle, gastrocnemius muscle, soleus muscle, quadriceps femoris muscle, gluteus maximus muscle, or rectus femoris muscle.

Embodiment 7: The method of embodiment 6, wherein the muscle location in the patient is a trapezius muscle.

Embodiment 8: The method of any one of embodiments 1-7, wherein the patient is injected with between 0.1 and 0.5 cc of saline solution at the muscle location.

Embodiment 9: The method of embodiment 8, wherein the patient is injected with 0.3 cc of saline solution at the muscle location.

Embodiment 10: The method of any one of embodiments 1-9, wherein the muscle location in the patient comprises a first location, the method further comprising:
(a) obtaining a pressure value for the patient from a second muscle location, wherein the pressure value is determined by inserting the needle of the device into a second muscle location in the patient, injecting saline solution into the patient at the second muscle location, and measuring a pressure value at the second muscle location;
(b) determining an average pressure value based on the pressure value measured at the first muscle location and the pressure value measured at the second muscle location; and
(c) diagnosing fibromyalgia in the patient if the average pressure value from the two muscle locations exceeds a threshold pressure value.

Embodiment 11: The method of embodiment 10, wherein the threshold pressure value is between 5 and 60, between 10 and 50, or between 20 and 40 millimeters of mercury (mmHg).

Embodiment 12: The method of embodiment 11, wherein the threshold pressure value is 20 millimeters of mercury (mmHg).

Embodiment 13: The method of any one of embodiments 1-12, further comprising:
using the measured pressure value at the muscle location to associate the patient with one of a plurality of muscle tenderness categories.

Embodiment 14: The method of embodiment 13, wherein the plurality of muscle tenderness categories comprises three categories of mild, moderate or extreme muscle tenderness.

Embodiment 15: The method of any one of embodiments 1-14, wherein the device includes:
(a) a syringe including the saline solution;
(b) a tube positioned between the syringe and the needle; and
(c) a pressure sensor configured to measure the pressure at the muscle location.

Embodiment 16: The method of any one of embodiments 1-15, wherein the needle comprises a first needle, and wherein the pressure value comprises a first pressure value, the method further comprising:
(a) providing a medication to the patient;
(b) obtaining a second pressure value from the patient from a second muscle location by inserting a second needle of the device into the second muscle location in the patient, injecting saline solution into the patient at the second muscle location, and measuring a second pressure value at the second muscle location; and
(c) comparing the first pressure value to the second pressure value to determine whether the pressure at the second muscle location has been reduced.

Embodiment 17: The method of embodiment 16, further comprising in response to a determination that the second pressure value at the second muscle location no longer exceeds the threshold pressure value, decreasing a dosage of the medication provided to the patient.

Embodiment 18: The method of embodiment 16, further comprising in response to a determination that the second pressure value at the second muscle location still exceeds the threshold pressure value, increasing a dosage of the medication provided to the patient.

Embodiment 19: The method of embodiment 16, further comprising in response to a determination that the second pressure value at the second muscle location still exceeds the threshold pressure value, maintaining a dosage of the medication provided to the patient.

Embodiment 20: The method of embodiment 16, wherein the medication comprises a muscle relaxant.

Embodiment 21: A method for treating fibromyalgia in a patient comprising:

(a) obtaining a pressure value for the patient, wherein the pressure value is determined by inserting a needle of a device into a muscle location in the patient, injecting saline solution into the patient at the muscle location, and measuring a pressure value at the muscle location; and (b) administering an effective amount of a muscle relaxant to the patient if the pressure at the muscle location exceeds a threshold pressure value.

Embodiment 22: The method of embodiment 21, wherein the needle has a gauge of between 10 and 30.

Embodiment 23: The method of embodiment 22, wherein the gauge of the needle is 22.

Embodiment 24: The method of any one of embodiments 21-23, wherein the threshold pressure value is between 5 and 60, between 10 and 50, or between 20 and 40 millimeters of mercury (mmHg).

Embodiment 25: The method of embodiment 24, wherein the threshold pressure value is 20 millimeters of mercury (mmHg).

Embodiment 26: The method of any one of embodiments 21-25, wherein the muscle location in the patient is a trapezius muscle, biceps brachii muscle, triceps brachii muscle, pectoralis major muscle, deltoideus muscle, gastrocnemius muscle, soleus muscle, quadriceps femoris muscle, gluteus maximus muscle, or rectus femoris muscle.

Embodiment 27: The method of embodiment 26, wherein the muscle location in the patient is a trapezius muscle.

Embodiment 28: The method of any one of embodiments 21-27, wherein the patient is injected with between 0.1 and 0.5 cc of saline solution at the muscle location.

Embodiment 29: The method of embodiment 28, wherein the patient is injected with 0.3 cc of saline solution at the muscle location.

Embodiment 30: A method of detecting a pressure value of a muscle location in a patient suspected of having fibromyalgia comprising:

(a) obtaining a pressure value for the patient, wherein the pressure value is determined by inserting a needle of a device into a muscle location in the patient, injecting saline solution into the patient at the muscle location, and measuring a pressure value at the muscle location; and (b) diagnosing fibromyalgia in the patient if the pressure at the muscle location exceeds a threshold pressure value.

Embodiment 31: The method of embodiment 30, wherein the needle has a gauge of between 10 and 30.

Embodiment 32: The method of embodiment 31, wherein the gauge of the needle is 22.

Embodiment 33: The method of any one of embodiments 30-32, wherein the threshold pressure value is between 5 and 60, between 10 and 50, or between 20 and 40 millimeters of mercury (mmHg).

Embodiment 34: The method of embodiment 33, wherein the threshold pressure value is 20 millimeters of mercury (mmHg).

Embodiment 35: The method of any one of embodiments 30-34, wherein the muscle location in the patient is a trapezius muscle, biceps brachii muscle, triceps brachii muscle, pectoralis major muscle, deltoideus muscle, gastrocnemius muscle, soleus muscle, quadriceps femoris muscle, gluteus maximus muscle, or rectus femoris muscle.

Embodiment 36: The method of embodiment 35, wherein the muscle location in the patient is a trapezius muscle.

Embodiment 37: The method of any one of embodiments 30-36, wherein the patient is injected with between 0.1 and 0.5 cc of saline solution at the muscle location.

Embodiment 38: The method of embodiment 37, wherein the patient is injected with 0.3 cc of saline solution at the muscle location.

Embodiment 39: A method for diagnosing and treating fibromyalgia in a patient comprising:

(a) obtaining a pressure value for the patient, wherein the pressure value is determined by inserting a needle of a device into a muscle location in the patient, injecting saline solution into the patient at the muscle location, and measuring a pressure value at the muscle location;

(b) diagnosing fibromyalgia in the patient if the pressure at the muscle location exceeds a threshold pressure value; and (c) administering an effective amount of a muscle relaxant to the diagnosed patient if the pressure at the muscle location exceeds a threshold pressure value.

Embodiment 40: The method of embodiment 39, wherein the needle has a gauge of between 10 and 30.

Embodiment 41: The method of embodiment 40, wherein the gauge of the needle is 22.

Embodiment 42: The method of any one of embodiments 39-41, wherein the threshold pressure value is between 5 and 60, between 10 and 50, or between 20 and 40 millimeters of mercury (mmHg).

Embodiment 43: The method of embodiment 42, wherein the threshold pressure value is 20 millimeters of mercury (mmHg).

Embodiment 44: The method of any one of embodiments 39-43, wherein the muscle location in the patient is a trapezius muscle, biceps brachii muscle, triceps brachii muscle, pectoralis major muscle, deltoideus muscle, gastrocnemius muscle, soleus muscle, quadriceps femoris muscle, gluteus maximus muscle, or rectus femoris muscle.

Embodiment 45: The method of embodiment 44, wherein the muscle location in the patient is a trapezius muscle.

Embodiment 46: The method of any one of embodiments 39-45, wherein the patient is injected with between 0.1 and 0.5 cc of saline solution at the muscle location.

Embodiment 47: The method of embodiment 46, wherein the patient is injected with 0.3 cc of saline solution at the muscle location.

Embodiment 48: A device, comprising:

a needle;

a syringe including a saline solution;

a tube positioned between the syringe and the needle; and a pressure sensor configured to obtain a pressure value at a muscle location of a patient.

Embodiment 49: The device of embodiment 48, wherein the needle has a gauge of between 10 and 30.

Embodiment 50: The device of embodiment 49, wherein the gauge of the needle is 22.

Embodiment 51: The device of any one of embodiments 48-50, wherein the muscle location in the patient is a trapezius muscle, biceps brachii muscle, triceps brachii muscle, pectoralis major muscle, deltoideus muscle, gastrocnemius muscle, soleus muscle, quadriceps femoris muscle, gluteus maximus muscle, or rectus femoris muscle.

Embodiment 52: The device of any one of embodiments 48-51, further comprising:

a display; and a control unit configured to:

provide for display the pressure value on the display.

Embodiment 53: The device of embodiment 52, wherein the control unit is further configured to:

compare the pressure value at the muscle location to a threshold pressure value;

provide for display an indication that the patient has fibromyalgia if the comparison indicates that the pressure value at the muscle location exceeds the threshold pressure value; and provide for display an indication that the patient does not have fibromyalgia if the comparison indicates that the pressure value at the muscle location does not exceed the threshold pressure value.

Embodiment 54: The device of embodiment 53, wherein the threshold pressure value is between 5 and 60, between 10 and 50, or between 20 and 40 millimeters of mercury (mmHg).

Embodiment 55: The device of embodiment 54, wherein the threshold pressure value is 20 millimeters of mercury (mmHg).

Embodiment 56: The device of any one of embodiments 52-55, wherein the control unit is further configured to:

use the measured pressure value at the muscle location to associate the patient with one of a plurality of muscle tenderness categories; and provide for display an indication of the associated muscle tenderness category.

Embodiment 57: The device of embodiment 56, wherein the plurality of muscle tenderness categories comprises three categories of mild, moderate, or extreme muscle tenderness.

Embodiment 58: The device of any one of embodiments 52-57, further comprising:

a drug delivery port positioned between the needle and the pressure sensor, wherein the drug delivery port is configured to provide a medicament to the muscle location through the needle.

Embodiment 59: The device of embodiment 58, wherein the medicament is a muscle relaxant.

Embodiment 60: The device of embodiment 58, wherein the control unit is further configured to:

administer an effective amount of a muscle relaxant to the patient through the drug delivery port if the pressure at the muscle location exceeds a threshold pressure value.

Embodiment 61: The device of embodiment 60, wherein the pressure value is a first pressure value, and wherein the control unit is further configured to:

obtain a second pressure value from the patient from the muscle location; and compare the first pressure value to the second pressure value to determine whether the pressure at the muscle location has been reduced.

Embodiment 62: The method of embodiment 61, wherein the control unit is further configured to:

in response to a determination that the second pressure value at the muscle location no longer exceeds the threshold pressure value, decreasing a dosage of the medication provided to the patient.

Embodiment 63: The method of embodiment 61, wherein the control unit is further configured to:

in response to a determination that the second pressure value at the muscle location still exceeds the threshold pressure value, increasing a dosage of the medication provided to the patient.

Embodiment 64: The method of embodiment 61, wherein the control unit is further configured to:

in response to a determination that the second pressure value at the muscle location still exceeds the threshold pressure value, maintaining a dosage of the medication provided to the patient.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

EXAMPLES

The Examples that follow are illustrative of specific embodiments of the invention, and various uses thereof. They are set forth for explanatory purposes only, and should not be construed as limiting the scope of the invention in any way.

Example 1. Muscle Pressure in Fibromyalgia Patients

The muscles are tender in fibromyalgia and the location of pain is generally over the muscles. Muscle pressure was measured in patients with fibromyalgia as well as in control patients.

Fibromyalgia patients meeting the 2010 American College of Rheumatology (ACR) criteria for the diagnosis were evaluated using a pressure gauge. The pressure gauge was attached to a 22 gauge needle, and 0.3 cc of saline was injected into the mid portion of the trapezius muscle of patients with fibromyalgia and also into normal control patients. The pressure in millimeters of mercury (mm Hg) was determined using this device. In addition, patients and controls had dolorimetry testing and manual compression of the trapezius muscles to determine the amount of tenderness.

In total, 103 fibromyalgia patients were evaluated (88 females and 15 males). The mean age of patients being evaluated was 52 years old for females and 47.5 years old for males. The mean dolorimetry score in the fibromyalgia patients was 8.1 pounds (0-30). The muscle pressure in fibromyalgia patients averaged 33 mmHg. The mean pain scale on a 1-10 visual analog scale (with 10 being the worst), was 7 in these fibromyalgia patients. Sixteen fibromyalgia patients had mild muscle tenderness, 52 had moderate muscle tenderness, and 30 had extreme muscle tenderness. In patients with mild muscle tenderness, the mean dolorimetry score was 11.8, mean muscle pressure reading was 28.7 mmHg, and the mean pain scale rating was 5. In the 52 fibromyalgia patients with moderate muscle tenderness over the trapezius muscle, the mean dolorimetry score was 7.9, the mean muscle pressure score was 33.9 mmHg, and the mean pain score was 6. In the fibromyalgia group with extreme muscle tenderness (30 patients with fibromyalgia), the mean dolorimetry score was 6.6, the mean muscle pressure reading was 35.5 mmHg, and the mean pain scale rating was 8. In a control group of 7 males and 18 females, the diagnoses included 15 with rheumatoid arthritis, 6 with systemic lupus, and 4 healthy office personnel. The mean dolorimetry score in this group was 21.2 (0-30). The mean muscle pressure was 12.2 mmHg. The mean pain scale was 2. Mild muscle tenderness was noted in one patient.

TABLE 2

Summary of results from muscle tension study in fibromyalgia patients.

| Reading | Average reading in Fibromyalgia patients (n = 103) | Average reading in Control patients (n = 25) |
|---|---|---|
| Dolorimetry score (pounds) | 8.1 | 21.2 |
| Muscle pressure (mmHg) | 33 | 12.2 |
| Pain scale (0-10, 10 being the worst pain imaginable) | 7 | 2 |
| Fibromyalgia patients (n = 16) with mild muscle tenderness dolorimetry score/muscle pressure/pain scale | 11.8/28.7/5 | — |
| Fibromyalgia patients (n = 52) with moderate muscle tenderness dolorimetry score/muscle pressure/pain scale | 7.9/33.9/6 | — |
| Fibromyalgia patients (n = 30) with extreme muscle tenderness dolorimetry score/muscle pressure/pain scale | 6.6/35.5/8 | — |

TABLE 3

Detailed results from muscle tension study in control patients.

| Number | Pain Scale 0 = no pain 10 = worst | Tenderness 0 = none 1 = mild 2 = moderate 3 = severe | Dolorimetry Score (pounds) | Muscle Pressure (mmHg) |
|---|---|---|---|---|
| 1 | 0 | 0 | 20.0 | 10.0 |
| 2 | 0 | 0 | 26.0 | 9.0 |
| 3 | 0 | 0 | 30.0 | 12.0 |
| 4 | 0 | 0 | 30.0 | 13.0 |
| 5 | 0 | 0 | 30.0 | 9.0 |
| 6 | 4 | 0 | 15.0 | 17.0 |
| 7 | 1 | 1 | 14.0 | 22.0 |
| 8 | 4 | 3 | 9.0 | 13.0 |
| 9 | 0 | 0 | 9.75 | 3.0 |
| 10 | 2 | 0 | 30.0 | 16.0 |
| 11 | 4 | 2 | 3.0 | 18.0 |
| 12 | 0 | 0 | 30.0 | 13.0 |
| 13 | 5 | 0 | 12.0 | 7.0 |
| 14 | 2 | 1 | 30.0 | 11.0 |
| 15 | 5 | 2 | 10.0 | 11.0 |
| 16 | 2 | 1 | 25.0 | 9.0 |
| 17 | 0 | 0 | 30.0 | 13.0 |
| 18 | 0 | 0 | 30.0 | 12.0 |
| 19 | 3 | 1 | 30.0 | 14.0 |
| 20 | 0 | 0 | 13.5 | 18.0 |
| 21 | 0 | 0 | 25.0 | 8.0 |
| 22 | 0 | 0 | 25.0 | 11.0 |
| 23 | 3 | 1 | 14.0 | 12.0 |
| 24 | 4 | 1 | 18.0 | 11.0 |
| 25 | 3 | 1 | 21.0 | 13.0 |

TABLE 4

Detailed results from muscle tension study in fibromyalgia patients.

| Number | Pain Scale 0 = no pain 10 = worst | Tenderness 0 = none 1 = mild 2 = moderate 3 = severe | Dolorimetry Score (pounds) | Muscle Pressure (mmHg) |
|---|---|---|---|---|
| 26 | 9 | 3 | 11.0 | 39.0 |
| 27 | 9 | 3 | 13.0 | 38.0 |
| 28 | 3 | 3 | 12.0 | 33.0 |
| 29 | 2 | 1 | 10.0 | 25.0 |
| 30 | 8 | 3 | 5.0 | 44.0 |
| 31 | 5 | 1 | 16.0 | 31.0 |
| 32 | 9 | 3 | 6.5 | 39.0 |
| 33 | 7 | 2 | 13.0 | 35.0 |
| 34 | 9 | 3 | 6.5 | 39.0 |
| 35 | 6 | 2 | 4.0 | 34.0 |
| 36 | 9 | 2 | 12.0 | 29.0 |
| 37 | 6 | 2 | 13.0 | 35.0 |
| 38 | 4 | 1 | 19.0 | 34.0 |
| 39 | 9 | 3 | 9.0 | 36.0 |
| 40 | 7 | 3 | 10.0 | 28.0 |
| 41 | 3 | 2 | 10.0 | 31.0 |
| 42 | 6 | 3 | 5.5 | 27.0 |
| 43 | 4 | 1 | 9.0 | 31.0 |
| 44 | 7 | 3 | 3.0 | 39.0 |
| 45 | 9 | 1 | 6.0 | 38.0 |
| 46 | 8 | 1 | 8.0 | 30.0 |
| 47 | 5 | 3 | 6.0 | 28.0 |
| 48 | 8 | 2 | 5.5 | 25.0 |
| 49 | 5 | 2 | 8.0 | 27.0 |
| 50 | 7 | 3 | 11.5 | 29.0 |
| 51 | 9 | 2 | 5.0 | 32.0 |
| 52 | 7 | 2 | 6.0 | 32.0 |
| 53 | 5 | 0 | 10.0 | 34.0 |
| 54 | 8 | 2 | 4.0 | 32.0 |
| 55 | 5 | 2 | 8.5 | 36.0 |
| 56 | 8 | 1 | 10.0 | 27.0 |
| 57 | 8 | 3 | 5.0 | 37.0 |
| 58 | 8 | 2 | 7.5 | 33.0 |
| 59 | 10 | 3 | 5.5 | 30.0 |
| 60 | 8 | 2 | 6.0 | 31.0 |
| 61 | 9 | 3 | 4.0 | 32.0 |
| 62 | 7 | 0 | 5.0 | 29.0 |
| 63 | 9 | 3 | 5.0 | 35.0 |
| 64 | 3 | 1 | 5.0 | 30.0 |
| 65 | 7 | 2 | 6.0 | 37.0 |
| 66 | 7 | 2 | 7.0 | 37.0 |
| 67 | 7 | 2 | 4.0 | 33.0 |
| 68 | 4 | 1 | 11.0 | 31.0 |
| 69 | 8 | 3 | 6.5 | 37.0 |
| 70 | 6 | 2 | 10.0 | 35.0 |
| 71 | 8 | 2 | 3.0 | 34.0 |
| 72 | 5 | 2 | 14.5 | 40.0 |
| 73 | 7 | 2 | 7.0 | 37.0 |
| 74 | 3 | 2 | 4.0 | 43.0 |
| 75 | 6 | 2 | 8.0 | 38.0 |
| 76 | 8 | 2 | 4.0 | 38.0 |
| 77 | 9 | 3 | 10.0 | 40.0 |
| 78 | 8 | 2 | 4.5 | 39.0 |
| 79 | 5 | 2 | 9.5 | 31.0 |
| 80 | 5 | 2 | 9.0 | 29.0 |
| 81 | 8 | 3 | 4.0 | 36.0 |
| 82 | 7 | 2 | 7.5 | 31.0 |
| 83 | 5 | 1 | 25.0 | 26.0 |
| 84 | 10 | 3 | 3.5 | 39.0 |
| 85 | 10 | 3 | 2.0 | 41.0 |
| 86 | 7 | 3 | 6.5 | 29.0 |
| 87 | 6 | 2 | 10.0 | 35.0 |
| 88 | 8 | 3 | 8.0 | 31.0 |
| 89 | 2 | 1 | 25.0 | 8.0 |
| 90 | 7 | 2 | 8.0 | 37.0 |
| 91 | 7 | 2 | 10.0 | 31.0 |
| 92 | 7 | 2 | 7.0 | 33.0 |
| 93 | 10 | 3 | 2.0 | 39.0 |
| 94 | 6 | 2 | 6.5 | 33.0 |
| 95 | 6 | 2 | 11.0 | 30.0 |
| 96 | 3 | 1 | 9.0 | 23.0 |
| 97 | 5 | 1 | 7.5 | 23.0 |

TABLE 4-continued

Detailed results from muscle tension study in fibromyalgia patients.

| Number | Pain Scale<br>0 = no pain<br>10 = worst | Tenderness<br>0 = none<br>1 = mild<br>2 = moderate<br>3 = severe | Dolorimetry<br>Score<br>(pounds) | Muscle<br>Pressure<br>(mmHg) |
|---|---|---|---|---|
| 98 | 6 | 2 | 6.5 | 31.0 |
| 99 | 5 | 2 | 4.5 | 31.0 |
| 100 | 10 | 3 | 4.5 | 38.0 |
| 101 | 8 | 2 | 10.0 | 23.0 |
| 102 | 8 | 3 | 6.5 | 39.0 |
| 103 | 6 | 2 | 7.0 | 36.0 |
| 104 | 8 | 2 | 4.0 | 38.0 |
| 105 | 8 | 3 | 3.0 | 34.0 |
| 106 | 5 | 2 | 14.5 | 40.0 |
| 107 | 8 | 2 | 6.0 | 31.0 |
| 108 | 8 | 3 | 8.0 | 30.0 |
| 109 | 6 | 2 | 10.0 | 33.0 |
| 110 | 6 | 2 | 6.5 | 29.0 |
| 111 | 6 | 2 | 4.0 | 41.0 |
| 112 | 9 | 3 | 4.0 | 43.0 |
| 113 | 6 | 1 | 14.0 | 22.0 |
| 114 | 6 | 2 | 7.5 | 34.0 |
| 115 | 7 | 2 | 12.5 | 33.0 |
| 116 | 8 | 2 | 6.5 | 32.0 |
| 117 | 4 | 2 | 8.0 | 36.0 |
| 118 | 4 | 1 | 5.0 | 58.0 |
| 119 | 8 | 2 | 16.0 | 37.0 |
| 120 | 5 | 2 | 9.5 | 29.0 |
| 121 | 5 | 2 | 12.0 | 37.0 |
| 122 | 4 | 2 | 8.0 | 27.0 |
| 123 | 9 | 3 | 9.0 | 35.0 |
| 124 | 8 | 2 | 7.0 | 34.0 |
| 125 | 7 | 3 | 4.0 | 36.0 |
| 126 | 7 | 2 | 6.5 | 42.0 |
| 127 | 8 | 2 | 6.0 | 36.0 |
| 128 | 4 | 1 | 10.0 | 23.0 |

Patients with fibromyalgia, compared to control patients, have significantly increased intramuscular pressure. Muscles in patients with fibromyalgia were also tender and dolorimetry scores were low indicating decreased tolerance for manually applied pressure. The amount of muscle tenderness correlated with the muscle pressure. The pain in fibromyalgia may be related to increased muscle pressure and tension. Fibromyalgia patients may be unconsciously tightening their muscles. Though pain centers in the brain light up quickly (central sensitization) in fibromyalgia patients when pressure is applied to the muscles, this finding may be due to increased muscle tenderness and elevated muscle pressure in fibromyalgia patients.

While the invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this application are expressly incorporated by reference herein.

What is claimed is:

1. A method for treating fibromyalgia in a patient comprising:
   (a) obtaining an intramuscular pressure value at a muscle location of the patient; and
   (b) administering an effective amount of a muscle relaxant to the patient when the intramuscular pressure value at the muscle location reaches a threshold value.

2. The method of claim 1, wherein the threshold value is between 5 and 60, between 10 and 50, or between 20 and 40 millimeters of mercury (mmHg).

3. The method of claim 2, wherein the threshold value is 20 millimeters of mercury (mmHg).

4. The method of claim 1, wherein the muscle location in the patient is a trapezius muscle, biceps brachii muscle, triceps brachii muscle, pectoralis major muscle, deltoideus muscle, gastrocnemius muscle, soleus muscle, quadriceps femoris muscle, gluteus maximus muscle, or rectus femoris muscle.

5. The method of claim 4, wherein the muscle location in the patient is the trapezius muscle.

6. The method of claim 1, wherein the muscle relaxant is baclofen, carisoprodol, chlorzoxazone, cyclobenzaprine, dantrolene, metaxalone, methocarbamol, orphenadrine, or tizanidine.

7. A method for treating fibromyalgia in a patient comprising:
   (a) obtaining an intramuscular pressure value at a muscle location of the patient; and
   (b) diagnosing fibromyalgia in the patient when the intramuscular pressure value at the muscle location reaches a threshold value; and
   (c) administering an effective amount of a muscle relaxant to the patient when the intramuscular pressure value at the muscle location reaches a threshold value.

8. The method of claim 7, wherein the threshold value is between 5 and 60, between 10 and 50, or between 20 and 40 millimeters of mercury (mmHg).

9. The method of claim 8, wherein the threshold value is 20 millimeters of mercury (mmHg).

10. The method of claim 7, wherein the muscle location in the patient is a trapezius muscle, biceps brachii muscle, triceps brachii muscle, pectoralis major muscle, deltoideus muscle, gastrocnemius muscle, soleus muscle, quadriceps femoris muscle, gluteus maximus muscle, or rectus femoris muscle.

11. The method of claim 10, wherein the muscle location in the patient is the trapezius muscle.

12. The method of claim 7, wherein the muscle relaxant is baclofen, carisoprodol, chlorzoxazone, cyclobenzaprine, dantrolene, metaxalone, methocarbamol, orphenadrine, or tizanidine.

* * * * *